United States Patent [19]

Yamamoto et al.

[11] Patent Number: 5,298,478
[45] Date of Patent: Mar. 29, 1994

[54] PRESERVATIVE FOR PLANTS COMPRISING DIPICOLINIC ACID

[75] Inventors: Kazuhiro Yamamoto; Noriko Yoshioka, both of Tokyo, Japan; Tadayasu Furukawa, Chesterfield, Mo.

[73] Assignee: Kyowa Hakko Kagyo Co., Japan

[21] Appl. No.: 991,030

[22] Filed: Dec. 15, 1992

Related U.S. Application Data

[62] Division of Ser. No. 831,262, Jan. 28, 1992, Pat. No. 5,171,351, which is a division of Ser. No. 507,332, Apr. 10, 1990, Pat. No. 5,112,380.

[30] Foreign Application Priority Data

Apr. 10, 1989 [JP] Japan .................................. 1-90379
Aug. 15, 1989 [JP] Japan ................................. 1-209666

[51] Int. Cl.$^5$ ........................... A01N 3/00; A01N 3/02
[52] U.S. Cl. .................................... 504/115; 426/310; 426/321
[58] Field of Search ............... 426/310, 321; 504/114, 504/115

[56] References Cited

U.S. PATENT DOCUMENTS

| 547,227 | 10/1895 | Pfitzer | 504/114 |
| 3,112,192 | 11/1963 | Feichtmer | 71/2.5 |
| 3,320,046 | 5/1967 | Siegal | 71/2.4 |
| 3,929,448 | 12/1975 | Brantley | 71/68 |
| 4,301,185 | 11/1981 | Schnell | 426/546 |
| 4,614,659 | 9/1986 | Liu | 426/321 |
| 4,710,388 | 12/1987 | Liu | 426/102 |
| 4,810,512 | 3/1989 | Kratky | 426/270 |

FOREIGN PATENT DOCUMENTS

| 0261422 | 3/1988 | European Pat. Off. . |
| 881299 | 10/1952 | Fed. Rep. of Germany . |
| 2540710 | 3/1977 | Fed. Rep. of Germany . |
| 45-115902 | 12/1970 | Japan . |
| 47-62749 | 6/1972 | Japan . |
| 48-43634 | 4/1973 | Japan . |
| 50-115334 | 9/1975 | Japan . |
| 52-107924 | 10/1977 | Japan . |
| 107924 | 4/1982 | Japan . |
| 57-207594 | 11/1982 | Japan . |
| 58-99432 | 6/1983 | Japan . |
| 60-118175 | 6/1985 | Japan . |
| 60-134794 | 6/1985 | Japan . |
| 60-280190 | 12/1985 | Japan . |
| 60-286779 | 12/1985 | Japan . |
| 61-8996 | 1/1986 | Japan . |
| 61-13421 | 1/1986 | Japan . |
| 61-38466 | 2/1986 | Japan . |
| 61-52179 | 3/1986 | Japan . |
| 61-57180 | 3/1986 | Japan . |
| 61-99023 | 4/1986 | Japan . |
| 61-181516 | 8/1986 | Japan . |
| 61-279392 | 11/1986 | Japan . |
| 62-48384 | 3/1987 | Japan . |
| 62-86633 | 4/1987 | Japan . |
| 63-240765 | 10/1988 | Japan . |
| 63-251073 | 10/1988 | Japan . |
| 1-61401 | 3/1989 | Japan . |
| 4-108601 | 4/1990 | Japan . |
| WO8802602 | 4/1988 | PCT Int'l Appl. . |
| 233509 | 4/1945 | Switzerland . |
| 1122662 | 8/1968 | United Kingdom . |
| 1229501 | 4/1971 | United Kingdom . |
| 1521912 | 8/1978 | United Kingdom . |
| 1527376 | 10/1978 | United Kingdom . |

OTHER PUBLICATIONS

Frenkel, C. "Regulation of Ripening in Bartlett Pears with Sulfhydryl Reagents" Bot. Gaz. 137(2): 154–159, 1976.

(List continued on next page.)

Primary Examiner—Richard L. Raymond
Assistant Examiner—S. Mark Clark
Attorney, Agent, or Firm—Pennie & Edmonds

[57] ABSTRACT

A preservative for plants is described whose active ingredient(s) are the compounds selected from the group consisting of olefin compounds and salts and esters thereof, N-(2-chloro-4-pyridyl)ureas, dipicolinic acid and derivatives and salts thereof, epoxy compounds and salts and esters thereof, and SH-reagents. The preservative is usable for keeping the freshness of plants, in particular fruits, vegetables and cut flowers, and cut flowers for a long period of time.

7 Claims, 13 Drawing Sheets

OTHER PUBLICATIONS

Sisler, et al. 1985, Physiol. Plant 63:114–120.
Sisler and Yang, 1984, Phytochemistry 23(12):2765–2768.
Frenkel, 1976, Bot. Gazette 137(2):154–159.
Pressman & Palevitch, 1973, HortScience 8(6):496–497.
Glamkowski, et al., 1970, J. Org. Chem. 35(10):3510–3512.
Kuraishi, et al., 1966, Plant and Cell Physiol. 7:705–706.
Richmond and Lang, 1957, Science 125:650–651.
Kiyoshi, O., 1987, Sizuoka University, Ann. Rpt. Farm Product Dist. Tech., p. 110–112.
Samejima et al., 1972, "Stabilization of Oils and Fats" Chemical Abstracts 77(3):418, Abstract #18427u 1972.
Bouchat and Golden, 1989, Antimicrobials Occuring Naturally in Food. Food Technology 43(1):at p. 140.
Mei, et al., 1989, Green Preservation Effects of 4PU-30 on Rice Leaves. Chemical Abstracts 110(23):279, Abstract #207726b.
Iliev, et al., 1985, Influence of Some Purine and Phenylurea Cytokinins and Atrazine on the Photochemical and Photosynthetic Activity in Aging Radish Leaves. Acta Univ. Agric., Fac. Agron. 33(3):449–451.
Forney, et al., 1982, Effects of Amino and Sulfhydryl Reactive Agents on Respiration and Ethylene Production in Tomato and Apple Fruit Discs. Physiol. Plant. 54:329–332.
Tochikubo, et al., 1967, Properties of Glucose Dehydrogenase from Vegetative Cells of *Bacillus subtilis* and the Effect of Dipicolinic Acid and its Chemical Analogues on the Enzyme. Japan J. Microbiol. 12(4):435–440.
Tabachnik-Ma'ayan and Fuchs, 1982, Free Sulfhydryl Groups in Ripening Fruits. Plant and Cell Physiol. 23(8)1309–1314.
Fields, M. L., 1973, Effect of Dipicolinate on Vegetative Cells of Bacillus. J. of Food Science 38:1166–1169.
Rao, et al., 1978, Prolonging Storage Life of Betal Leaves. Chemical Abstracts 88(7):167, Abstract #46245d.
Frenkel, C., 1976, Role of Auxin in the Hormonal Regulation of Fruit Ripening. Chemical Abstracts 84(8):119, Abstract #1163b.

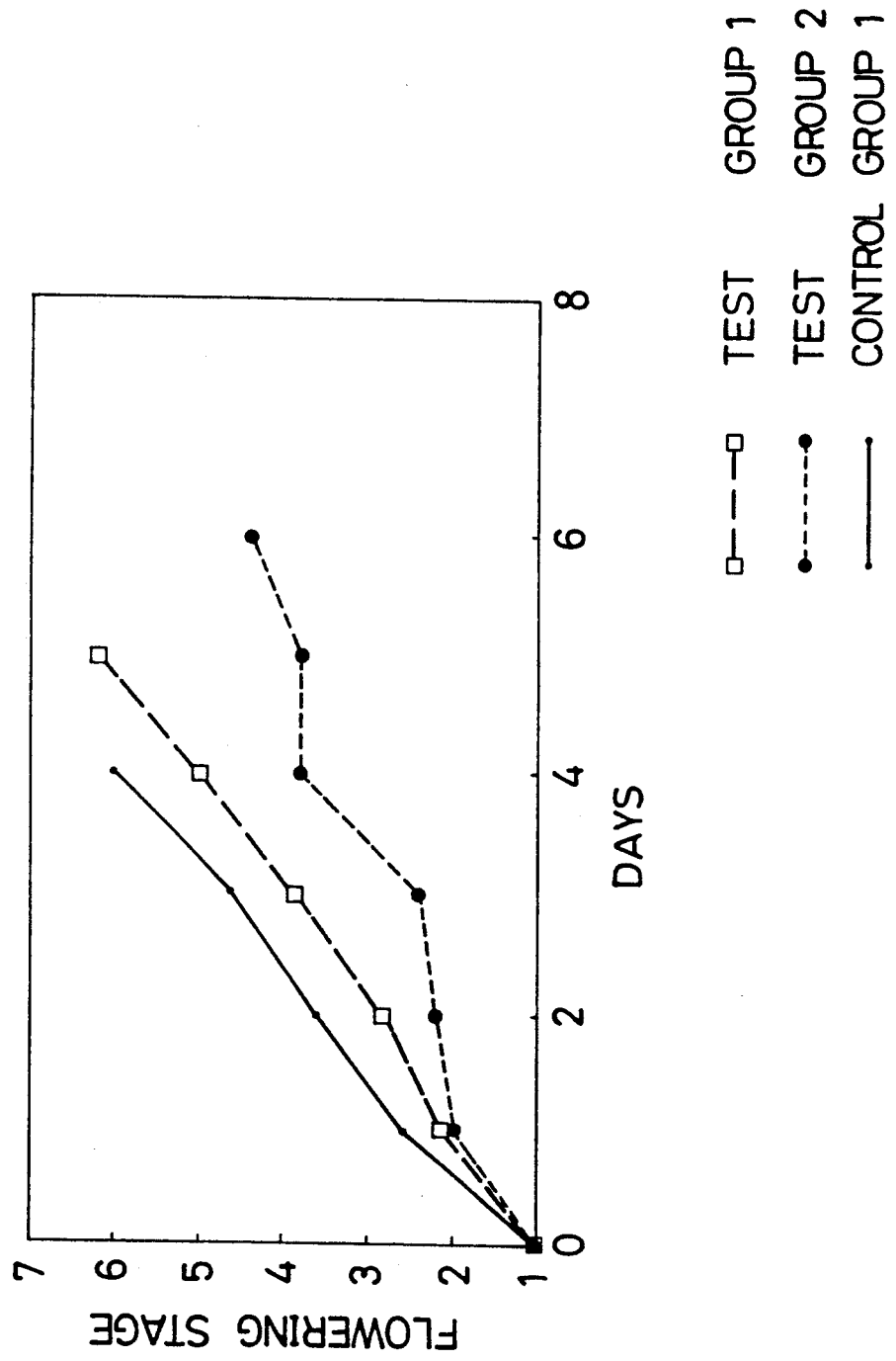

PRESERVATIVE FOR PLANTS COMPRISING DIPICOLINIC ACID

This is a division, of application Ser. No. 07/831,262, filed Jan. 28, 1992, now U.S. Pat. No. 5,171,351, which in turn is a division of Application Ser. No. 07/507,332 filed Apr. 10, 1990, currently U.S. Pat. No. 5,112,380.

FIELD OF THE INVENTION

The present invention relates to a preservative for plants, in particular fruits and vegetables, cut flowers, etc. after being harvested.

BACKGROUND OF THE INVENTION

Known conventional active ingredient(s) for keeping freshness of fruits and vegetables after being harvested include, as active ingredient(s) intended for keeping freshness of fruits and vegetables in general, e.g. organic or inorganic germanium (Patent Appln. Disclosure No. 293,338/86), biochemical energy source substances, such as sugar phosphate, amino acid phosphate, amidophosphate, hydroxy acid phosphate, adenosine phosphate, guanosine phosphate, creatine phosphate, etc. (JP-A-257,371/87), kojic acid (JP-A-198,372/87), extracts from Chlorella with hot water, and tocopherol and/or lecithin (JP-A-171,641/87), oligosaccharides (JP-A-214,120/88), vitamin C, salts of vitamin C and/or esters of vitamin C, and gallic acid, or its derivatives (JP-A-22,138/88) and, as active ingredient(s) intended for foods containing fruits and vegetables, lysozyme, ascorbic acid, glucose, and glucose oxidase (JP-A-143,672/87), chitin oligosaccharides, N-acetylglucosamine, glucosamine, salts of glucosamine and salts of chitosan (JP-A-39,569/88), hinokithiol included with cyclodextrin (JP-A-240,765/88), hexose phosphate ferrous salt, or divalent iron compound and hexose phosphate (JP-A-251,073/88) and, as active principles intended for fruits in general, calcium acetate and calcium lactate and/or sodium acetate (JP-A-143,635/87) and coffee bean cakes (JP-A-133,938/88) and, as active principles intended for strawberry, organic acids, such as malic acid, tartaric acid, etc. and lactose, sucrose, etc. (JP-A-41,255/77) and, as active principles intended for pear, basic amino acids and vitamin C (Japanese Patent Publication No. 6,341/80) and, as an active principle intended for pineapple, gibberellin (JP-A-231,944/86).

On the other hand, known active principles for keeping freshness of cut flowers include, e.g. silver thiosulfate, aluminum sulfate, 8-hydroxyquinoline sulfate, sugar, etc. (Nosanbutsu Ryutsu Gijyutsu Nenpo (Annual Report of Distribution Techniques for Agricultural Products), pp. 110–112 (1987)) and, as active principles intended for rose, metabolic sugars and phosphonic acids (JP-A-61,401/89), di-or trivalent basic organic carboxylic acids, and alkali salts thereof (JP-A-131,847/74), kinetin and 6-benzyladenine, which are a substance possessing a cytokinin activity (Science, 125 650–651, 1957, Plant & Cell Physiology 7 705–706, 1966, Hortscience 8 496–497, 1973), antiseptic/disinfectant (boric acid, chloride of lime, benzoic acid, salicylic acid, sorbic acid, dehydroacetic acid, propionic acid, isocyanuric acid, chlorous acid, hypochlorous acid, paraoxybenzoic acid, and esters thereof, lauryl trimethyl ammonium-2,4,5-trichloro-carbonilide, tribromosalicylateanilide, 3,4,4'-trichlorocarbonilide, hexachlorophene, bithionol, chloramine T, chloramine B halazon, etc.), nitrogen-containing compounds (urea, ammonium sulfate, ammonium chloride, ammonium carbamate, guanidine, alanine, glycine, chlorophyll, sodium nitrilo triacetate, etc.), phosphorus-containing compounds (polyphosphates, such as sodium tripolyphosphate, potassium pyrophosphate etc., and orthophosphate salts, such as monobasic sodium, monobasic potassium, monoammonium and dibasic sodium, dibasic potassium, and diammonium hydrogen phosphates, etc.), surface-active agents (anionic, cationic, or non-ionic surface-active agents), inorganic builders (sodium carbonate, potassium carbonate, ammonium carbonate, potassium sulfate, etc.), organic builders (citric acid, succinic acid, malic acid, tartaric acid, and gluconic acid and sodium salts thereof, pottasium salts thereof, ammonium salts thereof, etc.), solvents (monovalent or polyvalent lower alcohols, such as ethanol, propylene glycol, glycerol, etc.) (JP-A-24,750/74), 2-pyridinethiol-1-oxide (JP-A-98,001/84), ascorbic acid, isoascorbic acid, tryptophan, and thiourea (USP 3,320,046), kojic acid (JP-A-198,372/87), polylysine or its salts (JP-A-169,701/87), gallic acid or its derivatives (JP-A-22,138/88), and coffee bean cakes (JP-A-133,938/88).

At present, as preservatives for cut flowers, there is also customarily employed the preservative whose active ingredient(s) is silver thiosulfate. However, the problem of environmental pollution is worried, because silver included in the agents is a heavy metal. In addition, flowers to which the agents are effectively applied are limited to some types of flowers, such as carnation. Therefore, recently the development of a preservative demonstrating general effects which does not contain heavy metals has been desired.

There is known a case where cis-propenylphosphonic acid was employed as a synthetic precursor of phosphomycin which is one of antibiotics (J. of Organic Chemistry 35 3510–3512, 1970). In addition, it is a known case that 2,5-norbornadiene and cis-2-butene which are structural analogues of the cis-olefin compounds represented by the general formula (I) were used as materials for the study on plant-aging (Phytochemistry 23 2765–2768, 1984, PHYSIOLOGIA PLANTARUM 63 114–120, 1985). These compounds are in the form of gas at normal temperature under normal pressure, so that they are not practical.

The N-(2-chloro-4-pyridyl)ureas represented by the general formula (II) were developed as a synthetic plant hormone having a cytokinin activity and are known to show an excellent effect as a plant growth regulator (Patent Publication No. 16,104/82). In the past and present, these substances have been employed as agricultural chemicals for agriculture as well as gardening. Phosphomycin, one of the epoxy compounds represented by the general formula (III), is known in general as an antibiotic (Science, 166, 122, 1969), and already available on the market.

Dipicolinic acid and its derivatives have been employed as, e.g. a leaf-falling promoter (Patent Publication No. 44,858/73).

The object of the present invention provides preservative which show the excellent effects on plants after being harvested.

SUMMARY OF THE INVENTION

The present invention relates to a preservative for plants wherein active ingredient(s) are the compounds selected from the group consisting of olefin compounds represented by the general formula (I), or salts or esters thereof:

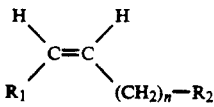

wherein $R_1$ stands for an alkyl group having from 1 to 3 carbon atoms, sulfo, phosphono, or hydroxyphenyl group, $R_2$ stands for a carboxyl, sulfo, phosphono, or hydroxyphenyl group, and n stands for an integer of 0 to 3, and from the group consisting of N-(2-chloro-4-pyridyl)ureas represented by the general formula (II):

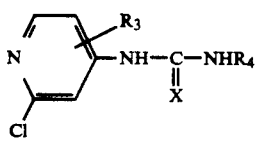

wherein $R_3$ stands for a hydrogen atom or a lower alkyl group, $R_4$ stands for an unsubstituted aromatic group, or an aromatic group substituted by a lower alkyl group, lower alkoxy, or hydroxy group or a halogen atom, and X stands for an oxygen or sulfur atom, and from the group consisting of dipicolinic acid, or its derivatives and salts, and epoxy compounds represented by the general formula (III), and salts and esters thereof:

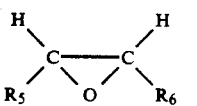

wherein $R_5$ stands for the same as $R_1$, and $R_6$ stands for the same as $R_2$, and SH-reagents including, but not limited to: N-ethylmaleimide, p-chloromercuribenzoic acid, p-chloromercuribenzene sulfonic acid, iodoacetic acid, and 5,5'-dithiobis(2-nitrobenzoic acid), etc.

According to the present invention, the freshness of freshly harvested fruits, vegetables, and portions of plants such as leaves, branches, cut flowers and the like can be maintained for periods of time greater than heretofore possible by treating the fruits, vegetables and the portions of plants with the preservatives described above.

For example, the treatment of vegetables such as broccoli with the preservatives can delay yellowing of the vegetables.

The treatment of cut flowers such as carnation and rose can prolong the life of flowers and can retard withering and wilting. Particularly, the treatment of rose can delay flower opening which results in the prolonging of the life.

BRIEF DESCRIPTION OF DRAWING

FIG. 13 shows changes of the stage in the flower opening of cut flowers tested in the Example 15.

DETAILED DESCRIPTION OF THE INVENTION

Figure 1:
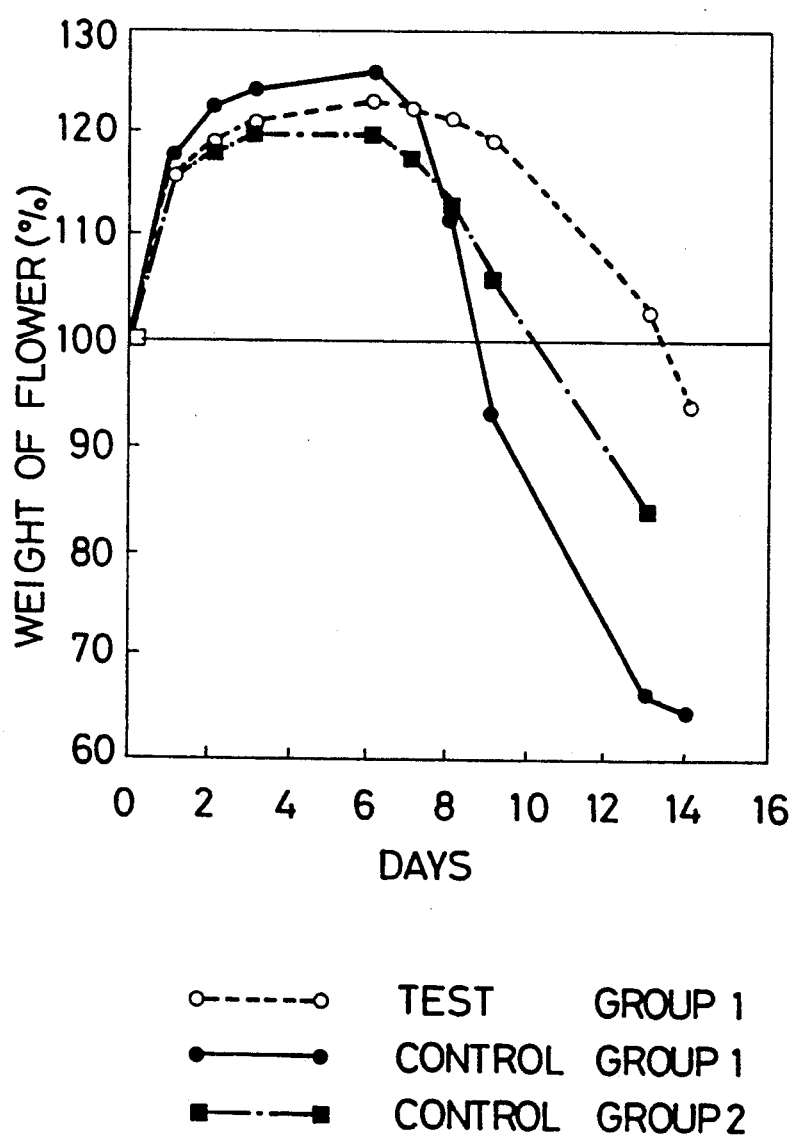
FIGS. 1 and 2 show the changes of weights of cut flowers tested in Examples 8 and 9, respectively, against the number of days.

The olefin compounds represented by the general formula (I) include crotonic acid, propenyl-1-sulfonic acid, propenyl-1-phosphonic acid, propenylphenol, 2-butenylphosphonic acid, 1-butenylphosphonic acid, 1-pentenylphosphonic acid, 1,2-diphosphonoethylene, propenyl-1,3-diphosphonic acid. These compounds include cis-form, trans-form and their mixture, and any of which can be used. In particular, cis-propenylphosphonic acid is preferred. There can be also used the alkali metal salts (sodium salts, potassium salts, etc.) or alkyl esters (methyl esters, ethyl esters, etc.) of the compounds represented by the general formula (I).

The N-(2-chloro-4-pyridyl)ureas represented by the general formula (II) include N-(2-chloro-4-pyridyl)-N'-phenylurea, N-(2-chloro-4-pyridyl)-N'-(m-chlorophenyl)urea, N-(2-chloro-4-pyridyl)-N'-(o-methylphenyl)urea, etc. Particularly, N-(2-chloro-4-pyridyl)-N'-phenylurea is preferable.

Derivatives of dipicolinic acid wherein the positions of two carboxyl groups are different include pyridine-2,5-dicarboxylic acid, and pyridine-2,4-dicarboxylic acid. In addition, their alkali salts (sodium salts, potassium salts, etc.) can be used. Epoxy compounds represented by the general formula (III) include phosphomycin.

The SH-reagents include N-ethylmaleimide, p-chloromercuribenzoic acid, p-chloromercuribenzene sulfonic acid, iodoacetic acid, and 5,5'-dithiobis (2-nitrobenzoic acid).

The preservative whose active ingredient(s) is a SH-reagent can be employed for cut flowers in particular.

All of the above-described active ingredient(s) are known compounds, and are in the form of a solid at normal temperature under normal pressure. For example, cis-propenylphosphonic acid represented by the general formula (I) is disclosed in JP-A-40,629/80 and in JP-A-52,299/83, and the N-(2-chloro-4-pyridyl)ureas represented by the general formula (II) are disclosed in Japanese Patent Publication No. 16,104/82. Both the dipicolinic acid and the SH-reagents are commercially available as a reagent.

These active ingredient(s) are employed in the form of a solution of various concentrations. Each of the concentration is not particularly limited since its optimum concentration differs depending on a type of plants to which the preservation is to be applied.

The concentration of olefin compounds represented by the formula (I), or salts thereof or esters thereof in a solution is in the range of 0.001 to 5 weight %. It is preferred that the concentration used is in the range of 0.1 to 2 weight % for application to fruits and vegetables, and 0.01 to 1 weight % for application to cut flowers. The used concentration of N-(2-chloro-4-pyridyl-)ureas represented by the general formula (II) in a solution is in the range of 0.01 to 50 ppm, preferably 1 to 10 ppm for fruits and vegetables, and 0.1 to 10 ppm for cut flowers.

The concentration of dipicolinic acid or its derivatives used in a solution is in the range of 0.001 to 1 weight %, preferably 0.01 to 0.5 weight %. The concentration of the epoxy compounds represented by the general formula (III) and salts and esters thereof in the solution is in the range of 0.001 to 5 weight %, preferably between 0.1 and 2 weight % for application to fruits and vegetables and between 0.01 and 1 weight % for application to cut flowers. The SH-reagent solution is used in the range of 1 to 1,000 ppm, preferably 5 to 50 ppm, in concentration.

The compounds can be used by being dissolved in a solvent, such as water, alcohols, etc., that can dissolve the compounds. It is preferred that they are used in the form of an aqueous solution.

As plants to which the preservatives of the present invention can be applied, fruits and vegetables include cabbage, lettuce, broccoli, asparagus, spinach, beaN sprouts, burdock, spring chrysanthemum, corn, carrot, cauliflower, Brussels sprout, bamboo shoot, parsley, broad bean, celery, green pepper, turnip, tomato, eggplant, cucumber, mushrooms, champignon, kabosu (*Citrus sphaerocarpa* Tanaka), sudachi, apple, pear, tangerine, strawberry, peach, pineapple, banana, grape, melon, avocado, etc. and cut flowers and potted plants include carnation, sweetpea, gypsophila, gerbera, rose, chrysanthemum, lily, stock, statice, gentian, gladiolus, Turkish bellflower, tulip, orchid, etc.

The preservatives of the present invention are preferably employed in the form of aqueous solution. The aqueous solution may be supplied to the plants by any convenient method such as spraying, immersing or drenching so long as the major portion of the plant.

A typical example of the treatment is immersion of the plant for one hour or more.

The preservatives of the present invention may also be used in powder or solid form. The powder or solid can be scattered on the plant or can put into a vase in which flowers are arranged.

The treatment of fruits or vegetables is usually carried out by immersing the same in a liquid form of preservative for 1 to 20 hours.

In a range so as not to spoil effects of the above-described active ingredient(s), other known preservatives can be added therein as necessary for use.

EXAMPLES

Example 1

Effect of preservative on yellowing of broccoli

Commercial broccoli was cut into 5 to 10 g small pieces. With buds facing down, 5 pieces were put in each of a 1 liter-beakers respectively containing 200 ml each of a 0.1 weight % aqueous cis-propenylphosphonic acid solution (test group 1); a 1 weight % aqueous cis-propenylphosphonic acid solution (test group 2); and tap water (control group 1), followed by being immersed therein for 1 hour.

After the water was removed softly, the pieces in each group were allowed to stand for 2 days in a 10-liter desiccater (a tray filled with water was placed therein).

Then, change in the color of the buds was observed with naked eye. In addition, by measuring with colorimeter each lightness (L) and chroma of the broccoli (a: green to red, b: blue to yellow) before and after they were allowed to stand, the difference in the color between before and after being allowed to stand was calculated therefrom and regarded as a measure of their green-fading and yellowing. (The higher $\Delta E$ indicates the progress of green-fading and yellowing. However, since the value is affected by lightness and chroma of plants before the test, it is regarded as a measure of change in the color of the buds for the Example only.)

$$\Delta E = \{(\Delta L)^2 + (\Delta b)^2 + (\Delta b)^2\}$$

$\Delta E$; difference in the color of the broccoli buds between before and after being allowed to stand $\Delta L$; difference in the "L" value between before and after being allowed to stand $\Delta a$; difference in the "a" value between before and after being allowed to stand $\Delta b$; difference in the "b" value between before and after being allowed to stand.

Results are shown in Table 1.

TABLE 1

| Test group and control group | After 2 days Appearance | $\Delta E^*$ |
|---|---|---|
| Test group 1 a 0.1 weight % aqueous cis-propenylphosphonic acid solution | Yellowing to some extent | 6.3 ± 0.8 |
| Test group 2 an 1 weight % aqueous cis-propenylphosphonic acid solution | Little yellowing Keeping green considerably | 4.5 ± 1.0 |
| Control 1 Tap water | Complete yellowing | 9.0 ± 1.8 |

*Average ± Standard Deviation

Example 2

Effect of preservative on yellowing of broccoli

The procedure was carried out in the same manner as in Example 1 except for the uses, as test groups, of an 1 ppm aqueous N-(2-chloro-4-pyridyl)-N'-phenylurea solution (test group 1) and a 10 ppm aqueous N-(2-chloro-4-pyridyl)-N'-phenylurea solution (test group 2) and, as control groups, of an 1 ppm aqueous 6-benzyladenine solution (control group 1), a 10 ppm aqueous 6-benzyladenine solution (control group 2), an 1 ppm aqueous kinetin solution (control group 3), a 10 ppm aqueous kinetin solution (control group 4), and tap water (control group 5).

Results are shown in Table 2.

TABLE 2

| Test group and control group | After 2 days Appearance | $\Delta E^*$ |
|---|---|---|
| Test group 1 an 1 ppm aqueous N-(2-chloro-4-pyridyl)-N'-phenylurea solution | No yellowing Keeping green perfectly | 1.3 ± 0.3 |

TABLE 2-continued

| Test group and control group | After 2 days Appearance | ΔE* |
|---|---|---|
| Test group 2 an 10 ppm aqueous N-(2-chloro-4-pyridyl)-N'-phenylurea solution | No Yellowing Keeping green perfectly | 1.1 ± 0.7 |
| Control 1 an 1 ppm aqueous 6-benzyladenine solution | Yellowing to some extent Green-fading to some extent | 3.6 ± 2.2 |
| Control 2 a 10 ppm aqueous 6-benzyladenine solution | Yellowing to some extent A little green-fading | 2.7 ± 1.0 |
| Control 3 an 1 ppm aqueous kinetin solution | A little yellowing Green-fading to some extent | 4.2 ± 1.2 |
| Control 4 a 10 ppm aqueous kinetin solution | A little yellowing Green-fading to some extent | 3.4 ± 0.8 |
| Control 5 Tap water | Complete yellowing | 10.3 ± 1.7 |

*Average ± Standard Deviation

EXAMPLE 3

Effect of preservative on yellowing of broccoli

The procedure was carried out in the same manner as in Example 1 except for the use, as test groups, of a 0.02 weight % aqueous dipicolinic acid solution (test solution (test and a 0.2 weight % aqueous dipicolinic acid solution (test group 2).

Results are shown in Table 3.

TABLE 3

| Test group and control group | After 2 days Appearance | ΔE* |
|---|---|---|
| Test group 1 a 0.02 weight % aqueous dipicolinic acid solution | Yellowing to some extent | 6.5 ± 1.2 |
| Test group 2 a 0.2 weight % aqueous dipicolinic acid solution | Little yellowing Keeping green considerably | 4.8 ± 0.6 |
| Control 1 Tap water | Complete yellowing | 9.2 ± 1.5 |

*Average ± Standard Deviation

Example 4

Preventive effect on withering of cut carnation flower

Carnations (*Dianthuscaryophyllus* L. cv. Coral) were cut in water to a lengths of 30 cm, immediately after harvest. The stems of the nine flowers were immersed, in each of a 200-ml Erlenmeyer flasks respectively containing 100 ml each of a 0.01 weight % aqueous cis-propenylphosphonic acid solution (test group 1); a 0.1 weight % aqueous cis-propenylphosphonic acid solution (test group 2); and tap water (control group 1). Then, they were allowed to stand at room temperature, and the degree of their withering was observed with the naked eye daily. Results are shown in Table 4. (Since the results are affected by some conditions, such as harvesting time of plants examined before the test, the degree of the withering progress is regarded as a measure for the Example only.)

TABLE 4

| Test group and control group | Days 0 | 4 | 8 | 12 | 16 |
|---|---|---|---|---|---|
| Test group 1 a 0.01 weight % aqueous cis-propenyl-phosphonic acid solution | − | − | − | − | + |
| Test group 2 a 0.1 weight % aqueous cis-propenyl-phosphonic acid solution | − | − | − | − | − |
| Control group 1 tap water | − | ± | + | ++ | +++ |

−: No withering,
±: Start of a little withering,
+: Obvious withering,
++: Almost complete withering,
+++: Putrefaction in addition to withering

Example 5

Preventive effect on withering of cut carnation flowers

Respective 5 carnations were treated in the same manner as in Example 4 except for the use, as test groups, of a 0.1 ppm aqueous N-(2-chloro-4-pyridyl)-N'-phenylurea solution (test group 1), an 1 ppm aqueous N-(2-chloro-4-pyridyl)-N'-phenylurea solution (test group 2), and an 1 ppm aqueous N-(2-chloro-4-pyridyl)-N'-(m-chloro-phenyl)urea solution (test group 3), and, as control groups, of an 1 ppm aqueous 6-benzyladenine solution (control group 1), an 1 ppm aqueous kinetin solution (control group 2), and tap water (control group 3).

Results are shown in Table 5.

TABLE 5

| Test group and control group | Days 0 | 2 | 4 | 6 | 8 |
|---|---|---|---|---|---|
| Test group 1 a 0.1 ppm aqueous N-(2-chloro-4-pyridyl)-N'-phenylurea solution | − | − | − | − | − |
| Test group 2 an 1 ppm aqueous N-(2-chloro-4-pyridyl)-N'-phenylurea solution | − | − | − | − | ± |
| Test group 3 an 1 ppm aqueous N-(2-chloro-4-pyridyl)-N'-(m-chloro-phenyl)urea solution | − | − | − | − | + |
| Control group 1 an 1 ppm aqueous 6-benzyladenine solution | − | − | − | ± | ++ |
| Control group 2 an 1 ppm aqueous kinetin solution | − | − | − | + | ++ |
| Control group 3 Tap water | − | ± | + | ++ | +++ |

−: No withering,
±: Start of a little withering,
+: Obvious withering,
++: Almost complete withering,
+++: Putrefaction in addition to withering

Example 6

Preventive effect on withering of cut carnation flowers

The procedure was carried out in the same manner as in Example 4 except for the use, as test groups, of a 0.2 weight % aqueous dipicolinic acid solution (test group 1), a 0.2 weight % aqueous pyridine-2,5-dicarboxylic acid solution (test group 2), and a 0.2 weight % aqueous pyridine-2,4-dicarboxylic acid solution (test group 3).

Results are shown in Table 6.

TABLE 6

| Test group and control group | Days | | | | |
|---|---|---|---|---|---|
| | 0 | 2 | 4 | 6 | 8 |
| Test group 1 a 0.2 weight % aqueous dipicolinic acid solution | − | − | − | − | − |
| Test group 2 a 0.2 weight % aqueous pyridine-2,5-dicarboxylic acid solution | − | − | − | ± | + |
| Test group 3 a 0.2 weight % aqueous pyridine-2,4-dicarboxylic acid solution | − | − | − | + | ++ |
| Control group 1 Tap water | − | ± | + | ++ | +++ |

−: No withering,
±: Start of little withering,
+: Obvious withering,
++: Almost complete withering,
+++: Putrefaction in addition to withering Example 7

Preventive effect on withering of cut carnation flowers

The tests were carried out in the same manner as in Example 4 except for the use, as test groups, of a 10 ppm aqueous N-ethylmaleimide solution (test group 1), a 10 ppm aqueous p-chloromercuribenzene sulfonic acid solution (test group 2), and a 10 ppm aqueous iodoacetic acid solution (test group 3).

Results are shown in Table 7.

TABLE 7

| Test group and control group | Days | | | | |
|---|---|---|---|---|---|
| | 0 | 4 | 8 | 12 | 16 |
| Test group 1 a 10 ppm aqueous N-ethylmaleimide solution | − | − | − | − | − |
| Test group 2 a 10 ppm aqueous p-chloromercuri-benzene sulfonic acid solution | − | − | − | − | ± |
| Test group 3 a 10 ppm aqueous iodoacetic acid solution | − | − | − | − | + |
| Control group 1 Tap water | − | ± | + | ++ | +++ |

−: No withering,
±: Start of a little withering,
+: Obvious withering,
++: Almost complete withering,
+++: Putrefaction in addition to withering Example 8

Preventive effect on withering of cut carnation flowers

Carnations (*Dianthus caryophyllus* L. cv. Coral) were cut in water to lengths of 30 cm, immediately after harvest. Then each cut flower was put in each of a 61 ml-test tubes respectively containing 30 ml each of an aqueous mixture solution of 1 weight % cis-propenyl-phosphonic acid, 0.2 weight % dipicolinic acid, and 10 weight % sucrose (test group 1), tap water (control group 1), and an aqueous solution of silver thiosulfate (0.1 mmol/l, control group 2) which is known to demonstrate a significant effect on delay withering of carnation, and the stem was immersed therein for 3 hours. Six cut flowers were used for one test group, respectively.

Then, all of the cut flowers were taken out from the respective immersing solutions, and the each flower was transferred to 61 ml-test tube containing 30 ml of tap water in each, and the flower was allowed to stand at room temperature. The degree of withering was observed with the naked eye daily, and the weight of the cut flowers was also measured.

Results are shown in Table 8 and FIG. 1.

TABLE 8

| Test group and control group | Vase life; the days until withering starts (mean of 6 flowers ± standard deviation) |
|---|---|
| Test group 1 1 weight % cis-propenyl-phosphonic acid 0.2 weight % dipicolinic acid 10 weight % sucrose | 11.7 ± 0.5 |
| Control group 1 Tap water | 6.3 ± 0.5 |
| Control group 2 a silver thiosulfate solution (0.1 mmol/l) | 11.2 ± 1.5 |

Example 9

Preventive effect on withering of cut carnation flowers

The procedure was carried out in the same manner as in Example 8 except for the use of "Yukon" as a cultivar of carnation.

Figure 2:
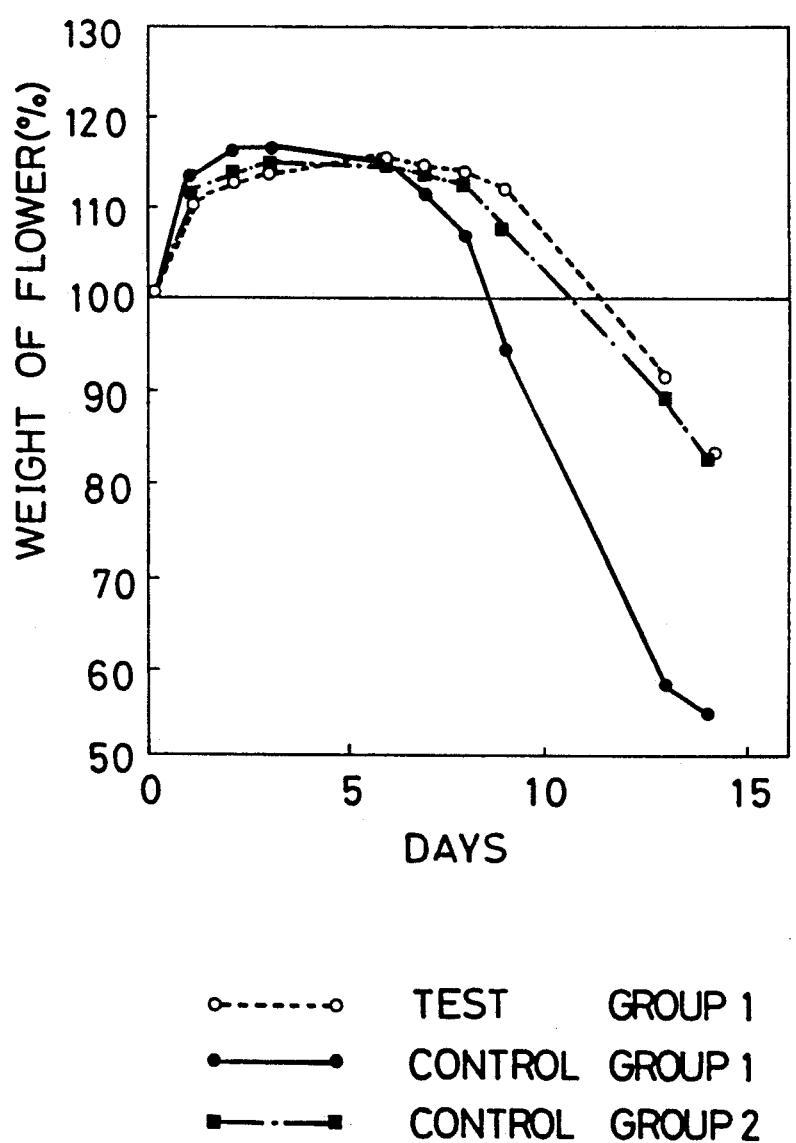

Results are shown in Table 9 and FIG. 2.

TABLE 9

| Test group and control group | Vase life; the days until withering starts (mean of 6 flowers ± standard deviation) |
|---|---|
| Test group 1 weight % cis-propenyl-phosphonic acid 0.2 weight % dipicolinic acid 10 weight % sucrose | 12.7 ± 0.8 |
| Control group 1 Tap water | 7.2 ± 1.0 |
| Control group 2 a silver thiosulfate solution (0.1 mmol/l) | 12.7 ± 2.1 |

Example 10

Preventive effect on withering of cut carnation flowers

The procedure was carried out in the same manner as in the Example 8 except for the use of "Arisetta" of a spray type as a cultivar of carnation and for the use, as test groups, of an aqueous mixture solution of 0.5 weight % cis-propenylphosphonic acid, 0.1 weight % dipicolinic acid, and 10 weight % sucrose and, as a control group, of tap water.

Results are shown in Table 10.

TABLE 10

| Test group and control group | Vase life; the days until withering starts (mean of 6 flowers ± standard deviation) |
|---|---|
| Test group 1 0.5 weight % cis-propenyl-phosphonic acid 0.1 weight % dipicolinic acid 10 weight % sucrose | 13.4 ± 2.6 |
| Control group Tap water | 7.0 ± 1.3 |

Example 11

Effect on prolonging the life of cut roses

Roses (*Rosa hibrida* L. cv. Sonia) were cut in water to lengths of 30 cm, immediately after harvested in the state of bud. The each cut flower was put in each of a 61 ml-test tubes respectively containing 30 ml each of a 0.01 weight % aqueous cis-propenylphosphonic acid solution (test group 1); an aqueous mixture solution of 0.01 weight % cis-propenylphosphonic acid and 3 weight % sucrose (test group 2), tap water (control group 1) and a commercial preservative for cut flower (a vase treatment agent "Hana no Sei" (Flower Sprite) made by Palace Chemical Corp., control group 2), to immerse its stem therein.

Then, they were allowed to stand in a room where the temperature and the relative humidity were adjusted to 20° C., 70%, respectively, and the stage in the flower opening and the external appearance of the flowers were observed with the naked eye daily. In addition, weight of the cut flowers as well as water uptake were measured.

Figure 3:
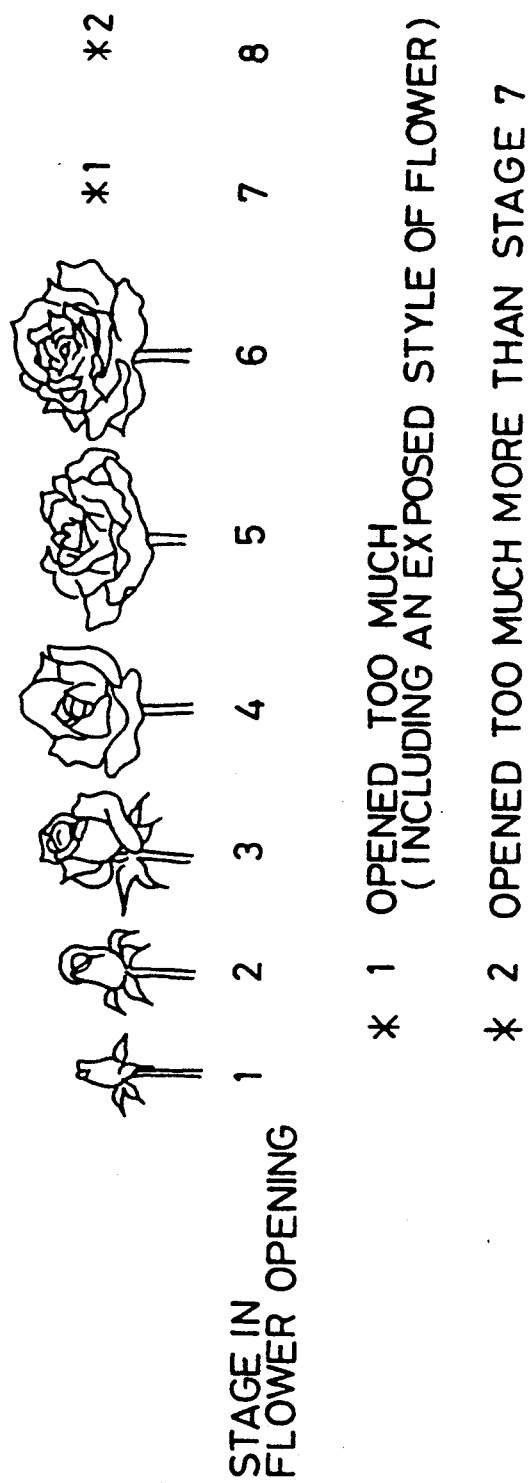
FIG. 3 is a figure wherein the change of the stage in the flower opening of cut rose flowers is expressed by numerical symbols.

The stage in the flower opening, as shown in FIG. 3, is expressed as numerical symbols, from the stage of the bud. The number in FIG. 3 indicates the stage in the flower opening. In the drawings, *1 means that the flower opened too much (including an exposed style of the flower), and *2 means that the flower opened too much more than stage 7.

As for the effect on prolonging the life of flower, flowers were judged to lose their ornamental values (the end point of flower) when two or more of five cut flowers tested showed their flowers apparently opened too much (including an exposed style of the flower), dropped of petals, withered, or drooped or a harmful effect of the chemical was shown, and then the observation and measurements were stopped.

Figure 4:
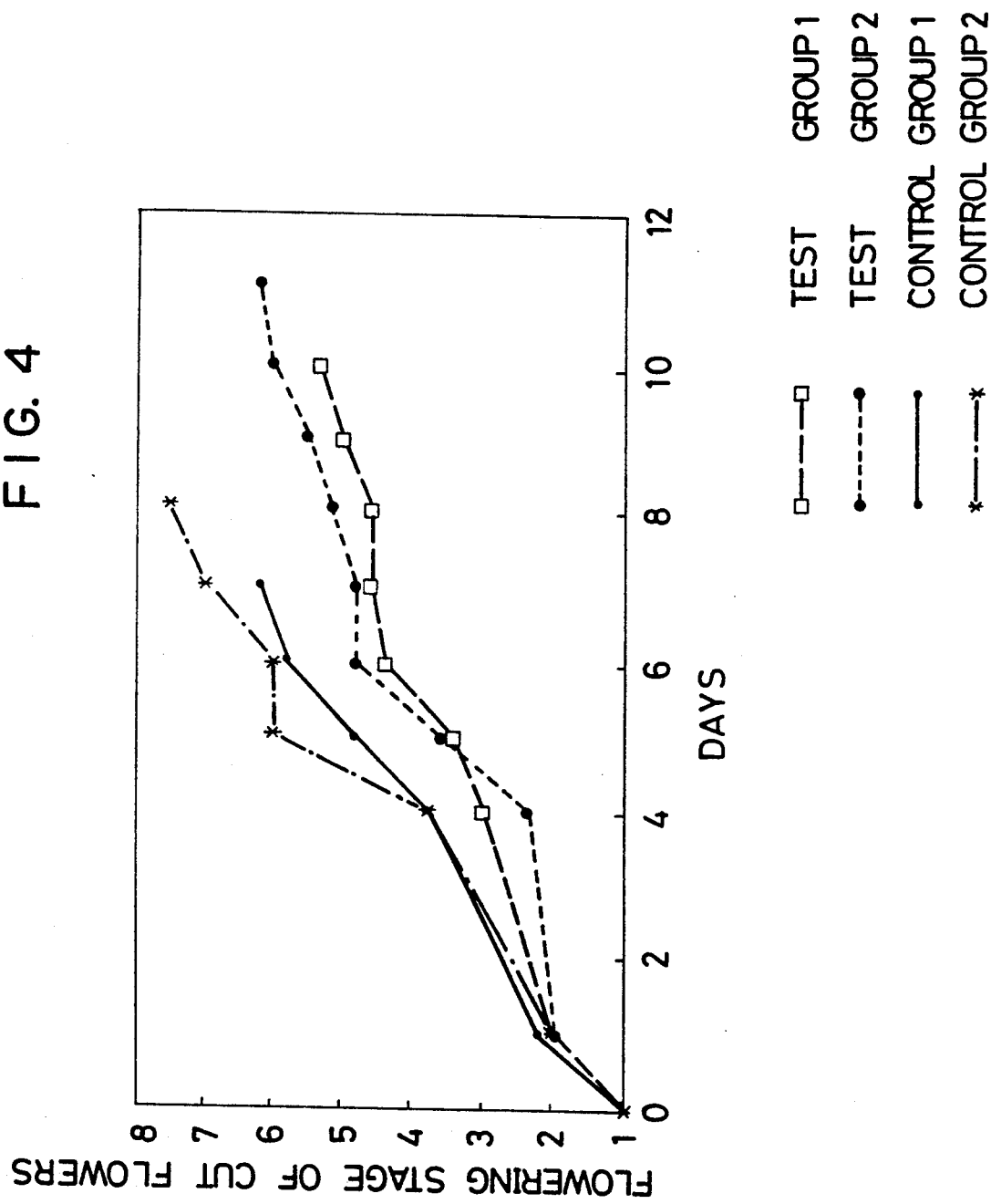
FIG. 4 shows the change of the stage in the flower opening of cut flowers tested in Example 11 against the number of days.
Figure 5:
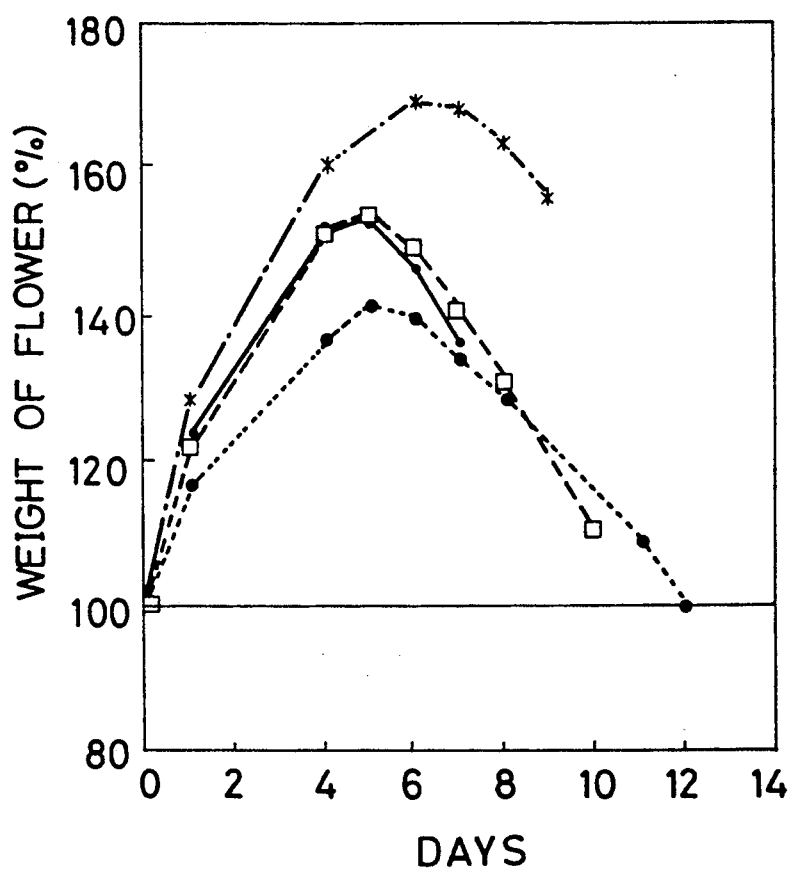
FIG. 5 shows the change of the weight % of cut flowers tested in Example 11 water uptake.
Figure 6:
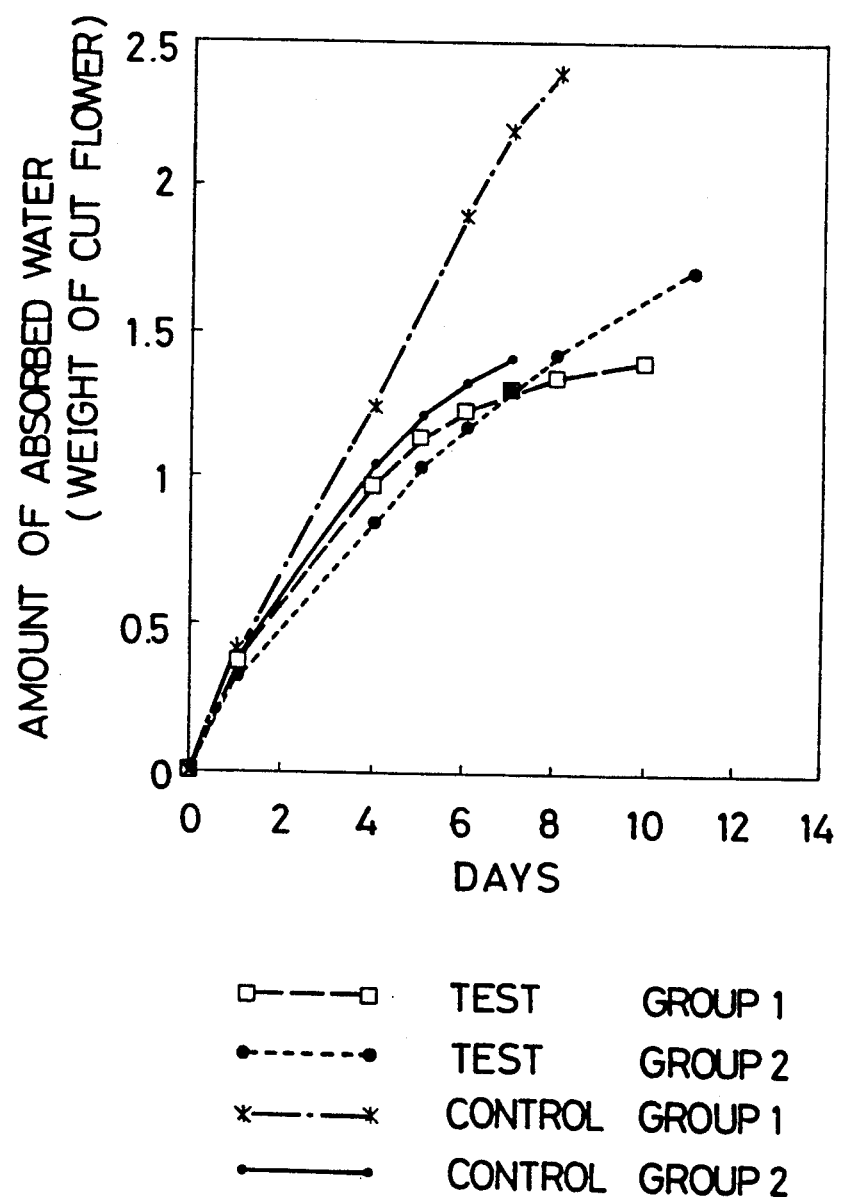
FIG. 6 shows the change of the water uptake (g/cut flower weight-g) by cut flowers tested in Example 11 against the number of days.

Results are shown in FIGS. 4, 5, and 6. The data in the figures in the drawing show mean values of five cut flowers.

Example 12

Effect on prolonging the life of cut roses

Roses (*Rosa hibrida* L. cv. Sonia) were cut in water to lengths of 30 cm, immediately after harvested in the state of bud. Then each cut flower was put in each of a 61 ml-test tubes respectively containing 30 ml each of a 0.01 weight % aqueous cis-propenylphosphonic acid solution (test group 1); a 0.05 weight % aqueous cis-propenylphosphonic acid solution (test group 2); or an aqueous mixture solution of 0.05 weight % cis-propenylphosphonic acid and 5 weight % sucrose (test group 3); and tap water (control group) to immerse the stem of the respective flowers for 20 hours therein.

Five cut flowers were employed for each of the test group. Then, all of the cut flowers were taken out from the each immersing solution, and then each flower was transferred to a 61 ml-test tube containing 30 ml of tap water, to immerse the stem, and was measured for the same items as in Example 11.

The above procedures were carried out in a room where the temperature and the relative humidity were adjusted to 20° C. and 70%, respectively.

Figure 7:
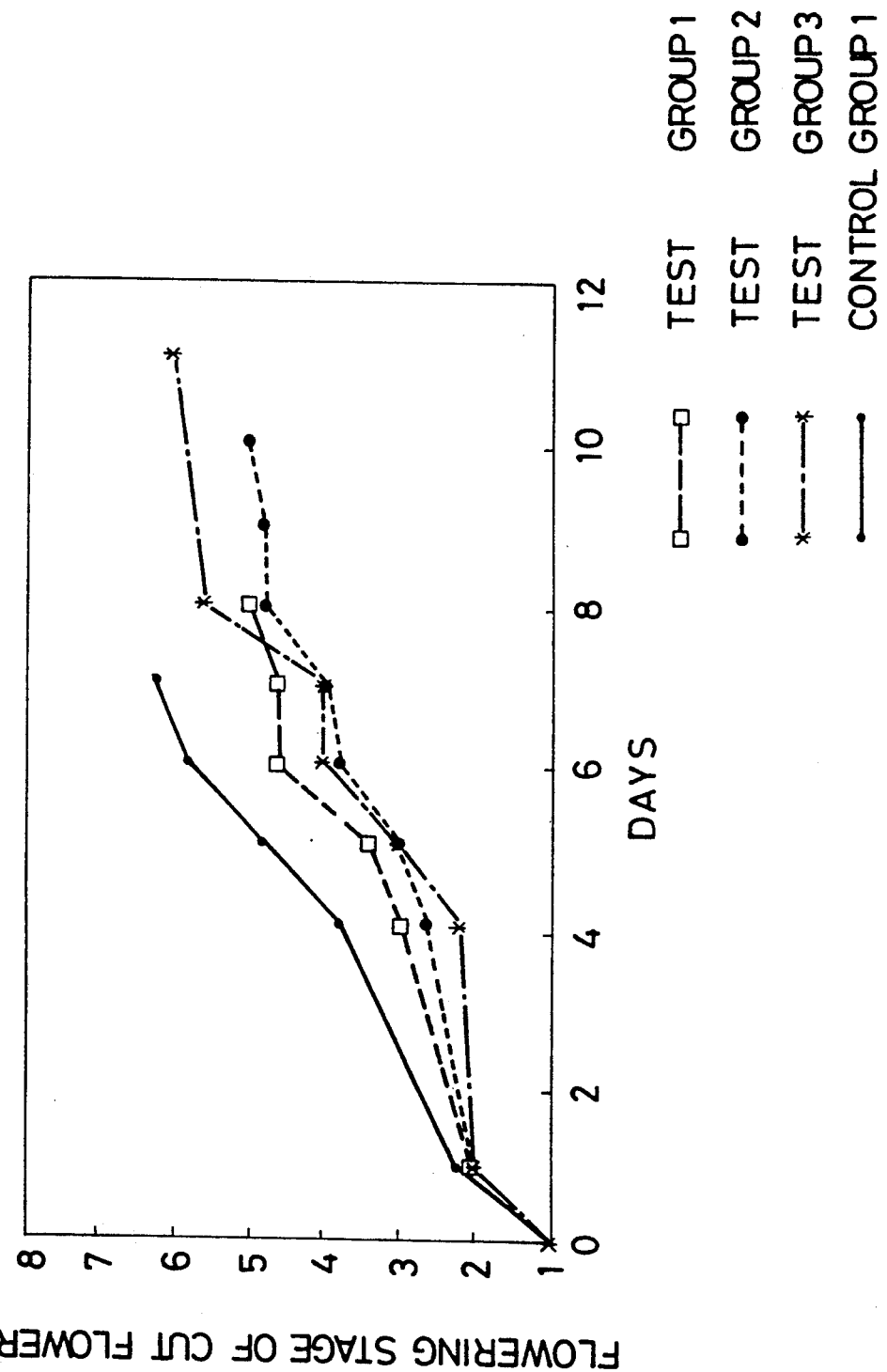
FIG. 7 shows the change of the stage in the flower opening of cut flowers tested in Example 12 against the number of days.
Figure 8:
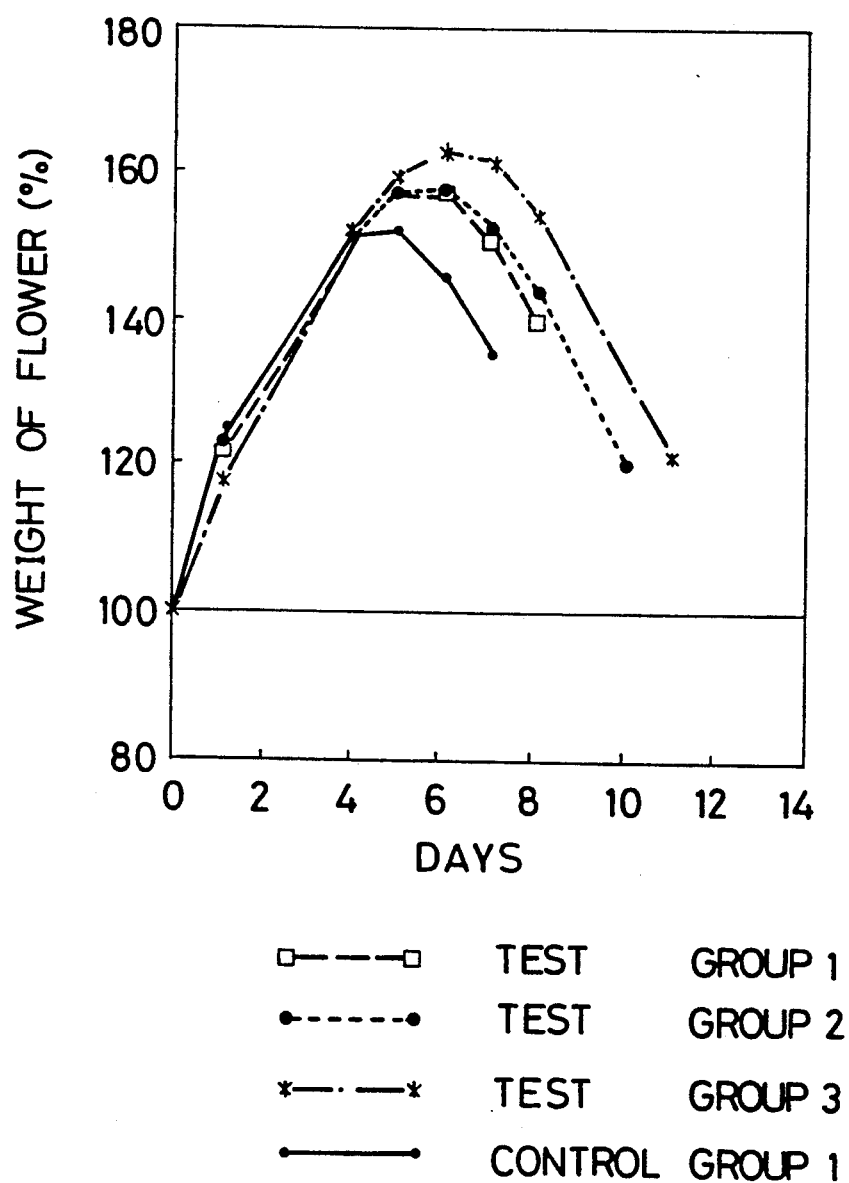
FIG. 8 shows the change of weight % of cut flowers tested in Example 12 against the number of days.
Figure 9:
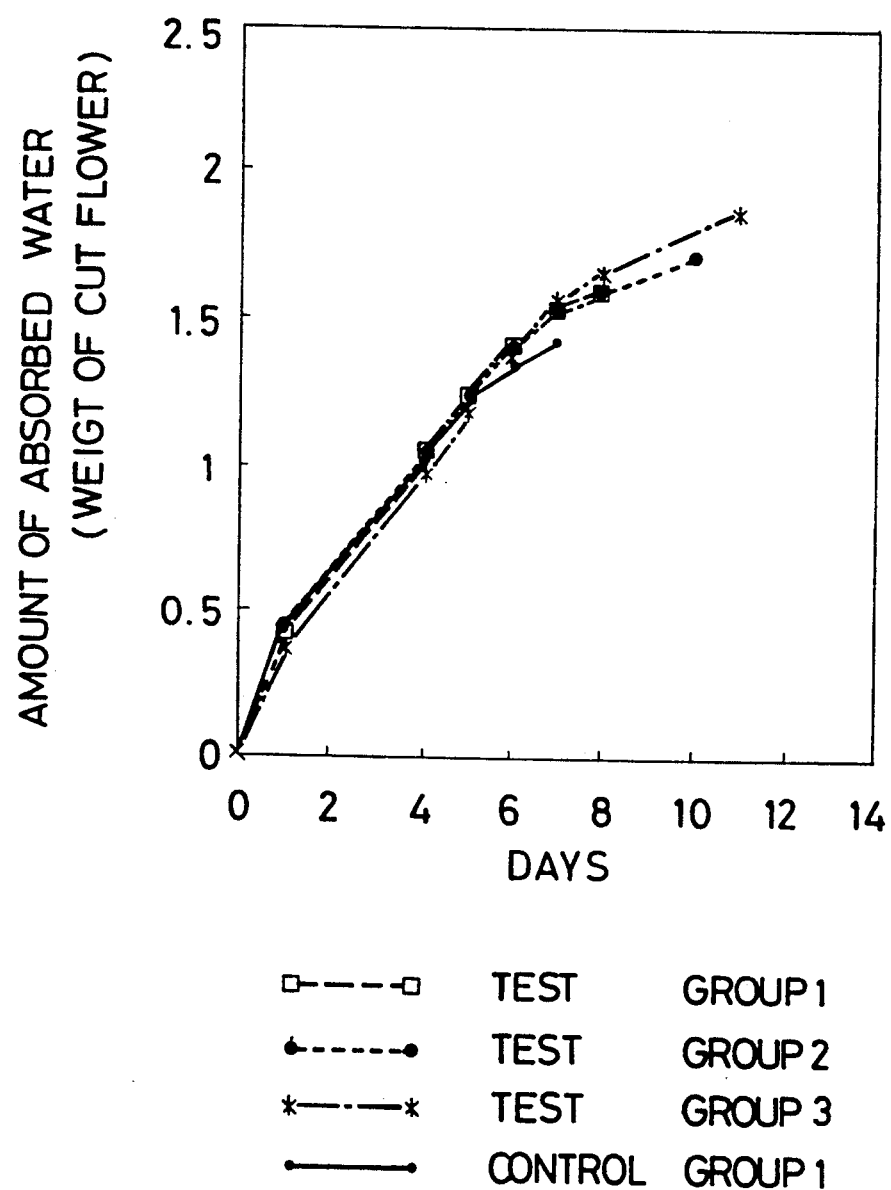
FIG. 9 shows the change of water uptake (g/cut flower weight-g) by cut flowers tested in Example 12 against the number of days.

Results are shown in FIGS. 7, 8, and 9. The data shown in FIGS. indicate mean values.

Example 13

Effect on prolonging the life of cut roses

Carina (*Rosa hibrida* L.) was employed as a cultivar of rose flower. The procedure was carried out in the same manner as in Example 12 except for the use of a 0.01 weight % aqueous cis-propenylphosphonic acid solution (test group 1), a 0.05 weight % aqueous cis-propenylphosphonic acid solution (test group 2), and tap water (control group 1) and the procedure was carried out in the same manner as in Example 11 except for the use of a commercial preservative [a vase treatment agent "Hana no Sei" (Flower Sprite), as control group 2].

Figure 10:
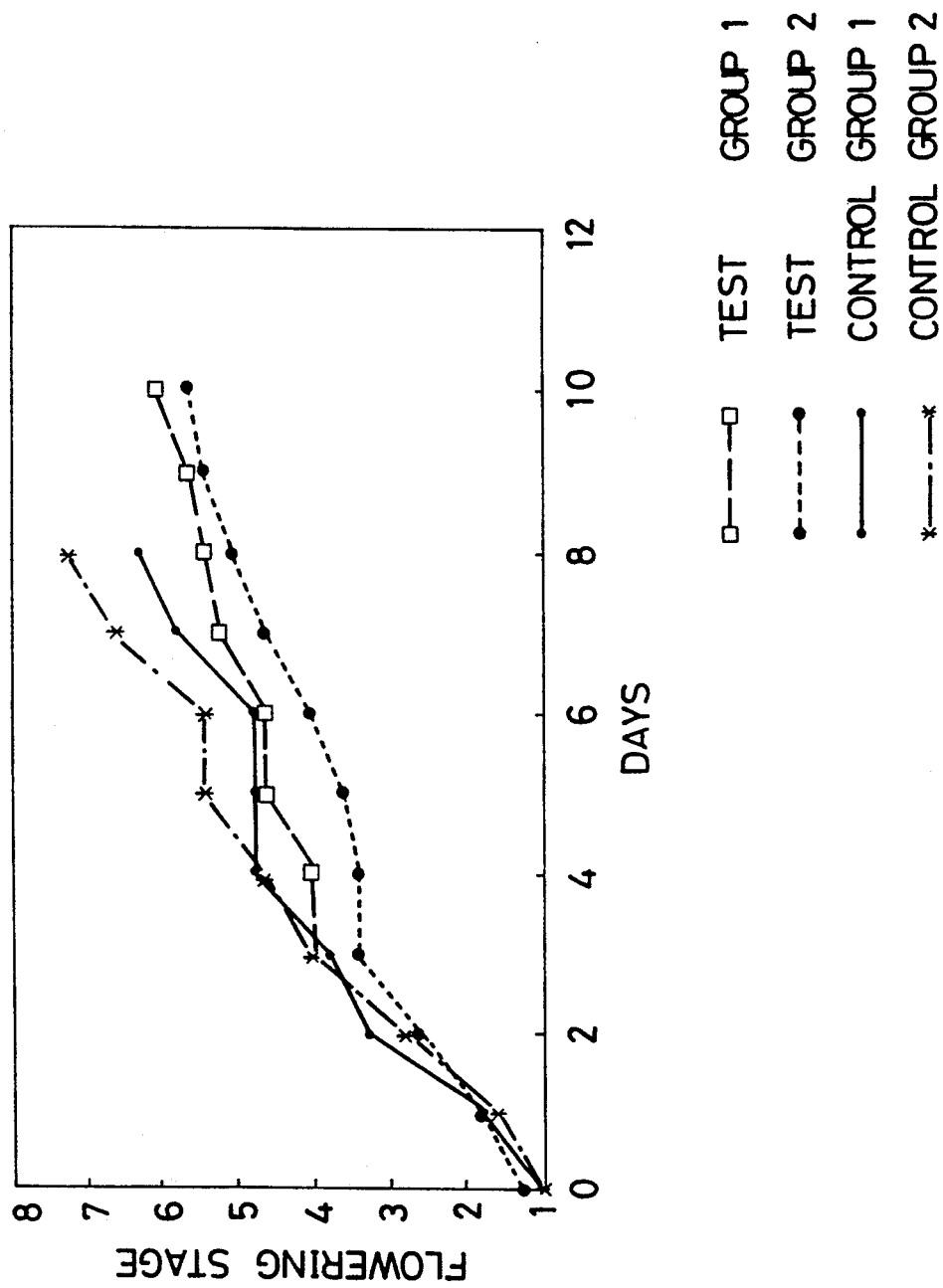
FIG. 10 shows the change of the stage in the flower opening of cut flowers tested in Example 13 against the number of days.

Results are shown in FIG. 10. The data in the figure indicate mean values of five cut flowers.

Example 14

Effect on prolonging the life of cut roses

The procedure was carried out in the same manner as in Example 11 except for the use, as a test group, of a 0.05 weight % aqueous cis-propenylphosphonic acid solution (test group 1), and the use, as control groups, of tap water (control group 1), a 0.01 weight % aqueous propenylphosphonic acid solution (control group 2), and a 0.05 weight % aqueous phenylphosphonic acid solution (control 3).

Figure 11:
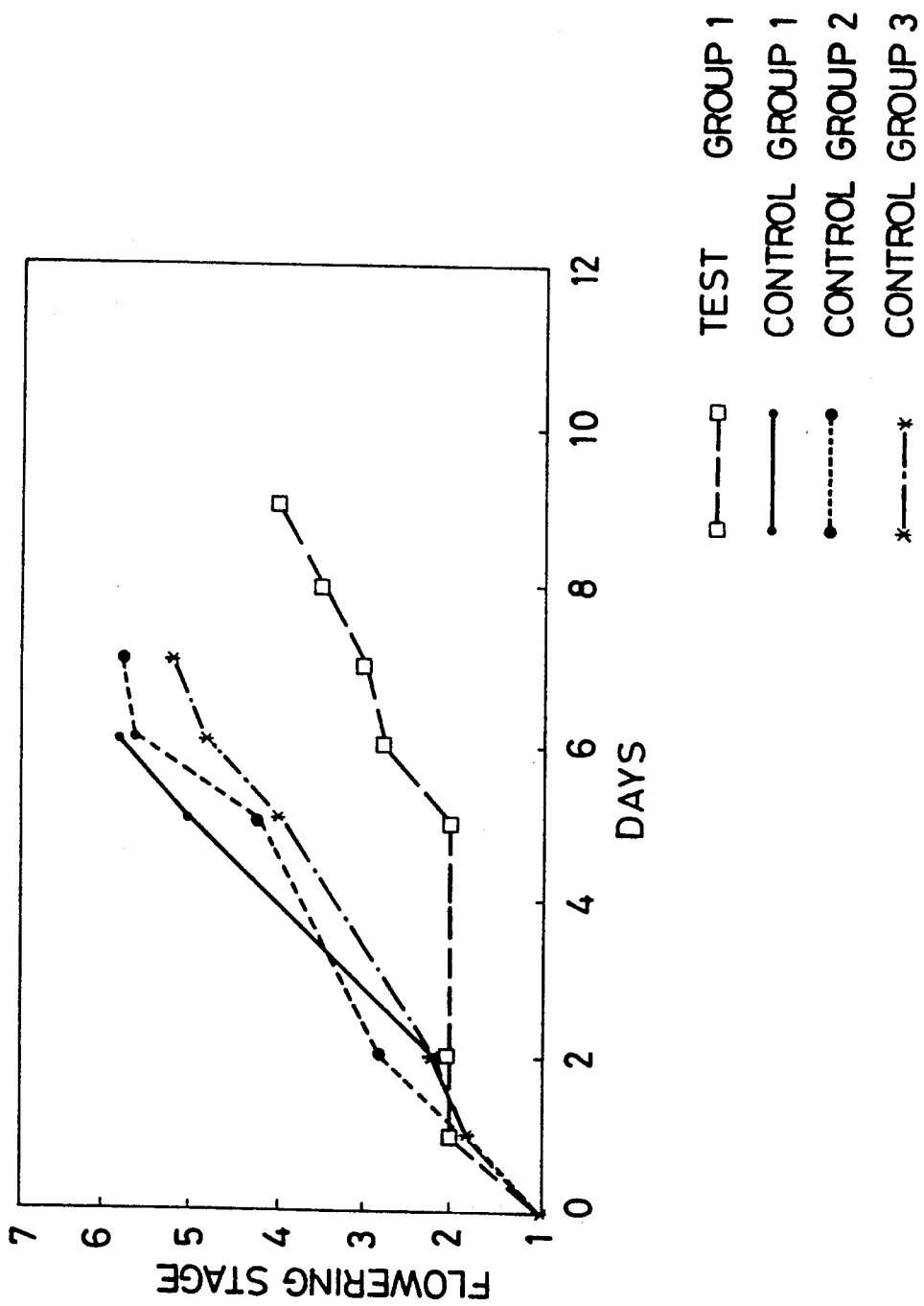
FIG. 11 shows the change of the stage in the flower opening of cut flowers tested in Example 14 against the number of days.
Figure 12:
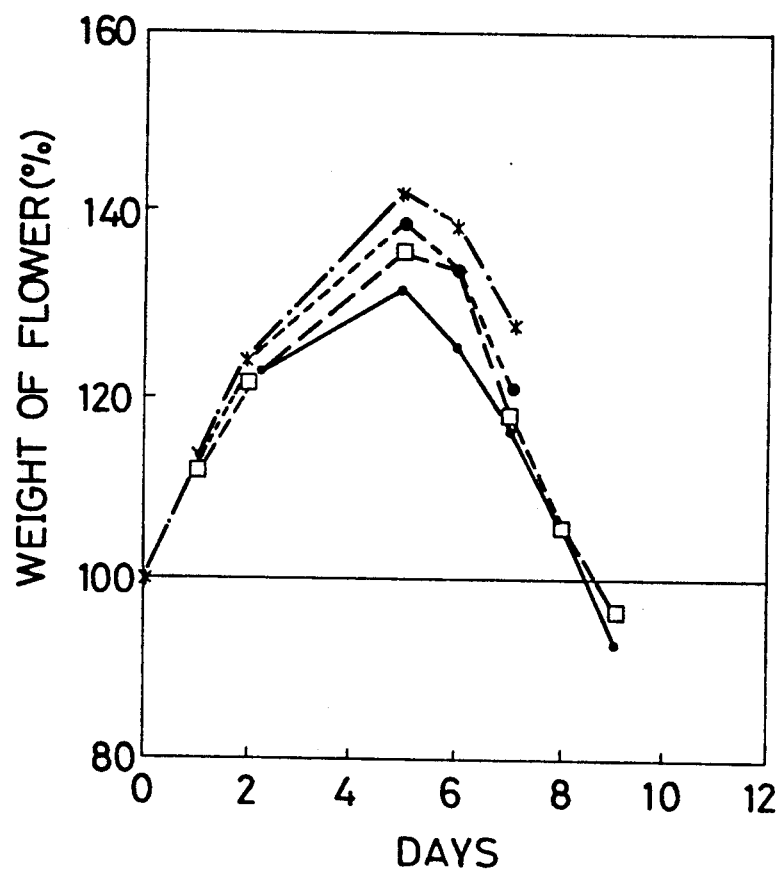
FIG. 12 shows the change of the weight % of cut flowers tested in Example 15 against the number of days.

Results are shown in FIGS. 11 and 12. The data indicated in the figures are mean values of five cut flowers.

Example 15

Effect on prolonging the life of cut roses

The procedure was carried out in the same manner as in Example 12 except for the use, as a test group, of 0.1 weight % aqueous solution of phosphomycin sodium salt (test group 1) and of 0.2 weight % aqueous solution of sodium salt of phosphomycin (test group 2).

Results are shown in FIG. 13. The data indicated in the figure are means value of five cut flowers.

Example 16

Preventive effect on withering of cut carnation flowers

The procedure was carried out in the same manner as in Example 4 except for the use, as a test group, of 0.4 weight % aqueous solution of phosphomycin sodium salt solution, and, as control groups, of tap water (control group 1) and of 0.4 weight % aqueous phenylphosphonic acid solution (control group 2). Results are shown in Table 11.

TABLE 11

| Test group and control group | Days | | | | |
|---|---|---|---|---|---|
| | 0 | 2 | 4 | 6 | 8 |
| Test group<br>0.4 weight % aqueous phosphymycin sodium salt solution | − | − | − | − | ± |
| Control group 1<br>Tap water | − | − | + | + | ++ |
| Control group 2<br>0.4 weight % aqueous phenylphosphonic acid solution | − | − | + | + | ++ |

−: No withering,
±: Start of a little withering,
+: Obvious withering
++: Almost complete withering

Example 17

Extended effect on vase life of cut tulip flowers

Commercially available tulip (type: pink supreme) was cut in water to lengths of into a 50 cm flower in length in water. Then each cut flower was put in each of a 61 ml-test tube respectively containing 30 ml each of an aqueous mixture solution of 0.1 weight % cis-propenylphosphonic acid (test group) and a tap water (control group). Three cut flowers were used for both the test group and the control group.

Thereafter all the cut flowers were allowed to stand in the same room with temperature and the relative humidity controlled at 20° C. and 70% respectively, and the appearance of each cut flower (petals, stems, etc.) was observed with the naked eye every day.

Results are shown in Table 12.

TABLE 12

| Test group and control group | Days | | | | |
|---|---|---|---|---|---|
| | 0 | 2 | 4 | 6 | 8 |
| Test group 0.1 weight % aqueous cis-propenylphosphonic acid solution | Normal | Normal | Normal | Normal | Normal |
| Control group Tap water | Normal | Normal | A bit bowing of stems | Bowing of stems, fallen petals | —* |

—*: Measurement ended at the sixth day, therefore no results are available.

What is claimed is:

1. A method for maintaining the freshness of a harvested plant or plant part which comprises treating the plant or plant part with a preservative containing dipicolinic acid or a derivative or salt thereof.

2. The method according to claim 1, wherein the plant or plant part is a fruit, a vegetable, a leaf, a branch, a flower, a root or a stem.

3. The method according to claim 1, wherein said harvested plant or plant part is a plant or plant part that has been severed from its natural growing environment and in which the severed plant or plant part is treated by contacting the severed portion thereof with said preservative.

4. The method according to claim 1, wherein said derivative of dipicolinic acid is pyridine-2,4-dicarboxylic acid or pyridine-2,5-dicarboxylic acid.

5. The method according to claim 1, where said plant is broccoli.

6. The method according to claim 3, wherein said plant part is a cut flower.

7. The method according to claim 6, in which the cut flower is a carnation.

* * * * *